United States Patent
Bhamidipati et al.

(10) Patent No.: US 8,609,876 B2
(45) Date of Patent: Dec. 17, 2013

(54) 9,10,12-TRIACYLOXY OCTADECANOIC ACID ALKYL ESTER AND 9,10,12-TRIACYLOXY OCTADECANOIC ACID ALKYL ESTER RICH FATTY ACID ALKYL ESTERS MIXTURE AND A PROCESS FOR PREPARATION THEREOF

(75) Inventors: Venkata Surya Koppeswara Rao Bhamidipati, Hyderabad (IN); Venkata Padmaja Korlipara, Hyderabad (IN); Karunakar Reddy Rondla, Hyderabad (IN); Satya Bhaskar Potula, Hyderabad (IN); Saravanan Krishnasamy, Hyderabad (IN); Badari Narayana Prasad Rachapudi, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 380 days.

(21) Appl. No.: 12/992,503

(22) PCT Filed: May 14, 2009

(86) PCT No.: PCT/IN2009/000287
§ 371 (c)(1),
(2), (4) Date: Jan. 28, 2011

(87) PCT Pub. No.: WO2009/139006
PCT Pub. Date: Nov. 19, 2009

(65) Prior Publication Data
US 2011/0124896 A1 May 26, 2011

(30) Foreign Application Priority Data
May 14, 2008 (IN) .......................... 1200/DEL/2008

(51) Int. Cl.
*C07C 51/00* (2006.01)
*C07C 59/00* (2006.01)

(52) U.S. Cl.
USPC ........................ 554/213; 554/124; 554/227

(58) Field of Classification Search
None
See application file for complete search history.

(56) References Cited

FOREIGN PATENT DOCUMENTS

JP 04-128256 * 4/1992 ............ C07C 235/08

OTHER PUBLICATIONS

Mostafa, M., et al., Composition of oil from the seeds of Cassia Sophera Linn, 2007, Bangladesh J. Sci. Ind. Res., 42(1), pp. 75-78.*

Knight, H.B., et al., Esters of Hydroxysteric acids as primary low-temperatue plasticizers for vinyl chloride-vinyl acetate copolymer, Sep. 1959, The Journal of the American Oil Chemists' Society, vol. 36, pp. 382-388.*
S. J. Randles et al. "Environmentally Considerate Ester Lubricants for the Automotive and Engineering Industries," JSL 9-2 145-161, 1992.
P. V. Joseph et al. "Study of some non-edible vegetable oils of Indian origin for lubricant application," Journal of Synthetic Lubrication, 24: 181-197 (2007).
S. Asadauskas et al. "Oxidative Stability and Antiwear Properties of High Oleic Vegetable Oils," Lubrication Engineering, vol. 52, 12, 877-882, (1996).
K. T. Achaya "Chemical Derivatived of Castor Oil," The Journal of the American Oil Chemists' Society. vol. 48,759-763, (1971).
M. G. Kulkarni et al. "Some physical properties of castor oil esters and hydrogenated castor oil esters," Eur. J. Lipid Sci. Technol. 105, 214-218, (2003).
J. Cvengros et al. "Properties of alkyl esters base on castor oil," Eur. J. Lipid Sci. Technol. 108, 629-635, (2006).
T. Di-Hua et al. "Modification of the Chemical Structure of an Environmentally-Friendly Castor Oil Lubricant," J. Synthetic Lubrication 21-1,59-63 (2004).
Kalantar et al. "Transformations of Hydroxy Cyclic Sulfates: Stereospecific Conversion into 2,3,5-Trisubstituted Tetrahydrofurans," Acta Chemica Scandinavica 47, 307-313, (1993).
E. D. Mihelich "Structure and Stereochemistry of Novel Endoperoxides Isolated from the Sensitized Photooxidation of Methyl Linoleate. Implications for Prostaglandin Biosynthesis," J. Am. Chem Soc. 102, 7141-7143, (1980).
F. H. Stodola "Base-Catalyzed Preparation of Methyl and Ethyl Esters of Carboxylic Acids," Microchem. J. vol. 29, 9, 389, 2940-2941, (1963).

* cited by examiner

*Primary Examiner* — Yate K Cutliff
(74) *Attorney, Agent, or Firm* — Edwards Wildman Palmer LLP; Barry Kramer; Nicholas J. DiCeglie, Jr.

(57) ABSTRACT

The present invention relates to modification of the chemical structure of ricinoleic acid, which is present to an extent of 85-90% in castor oil into triacyloxy alkyl ester derivatives. Accordingly, 9,10,12-trihydroxy octadecanoic acid rich fatty acid mixture was prepared from castor oil and converted to their alkyl esters followed by acylation of hydroxy groups to get 9,10,12-triacyloxy octadecanoic acid alkyl ester rich fatty acid alkyl esters mixture. The 9,10,12-triacyloxy octadecanoic acid alkyl esters were purified from the crude product and characterized by $^1$H NMR studies. The crude products were also evaluated for acid value (A.V.), hydroxyl value (H. V.), iodine value (I. V.), viscosity, viscosity index (V.I.), pour point, flash point and copper strip corrosion and found to be potential base stocks for hydraulic, metal working fluids and other industrial fluids.

12 Claims, No Drawings

9,10,12-TRIACYLOXY OCTADECANOIC ACID ALKYL ESTER AND 9,10,12-TRIACYLOXY OCTADECANOIC ACID ALKYL ESTER RICH FATTY ACID ALKYL ESTERS MIXTURE AND A PROCESS FOR PREPARATION THEREOF

Cross reference to related applications:

This application is a U.S. National Stage application under 35 U.S.C. §371 of International Patent Application Serial No. PCT/IN2009/000287, filed May 14, 2009 and Amended Under PCT Article 19 on Oct. 30, 2009, which claims the benefit of the Indian Patent Application No. 1200/DEL/2008, filed May 14, 2008, the disclosures of each of which are expressly incorporated by reference in their entireties.

FIELD OF THE INVENTION

This invention relates to a novel chemically modified castor oil fatty acid compounds namely 9,10,12-tri hydroxy octadecanoic acid alkyl ester rich fatty acid alkyl esters and 9,10, 12-tri acyloxy octadecanoic acid alkyl ester rich fatty acid alkyl esters mixture having superior lubricant performance properties and the methods for their preparation

BACKGROUND OF THE INVENTION

Vegetable oils such as rapeseed oil and high oleic varieties of oils are considered to be potential candidates to prepare bio-lubricant feed stocks which replace conventional mineral oil based lubricating oils and synthetic esters [Randles, S. J. et al.; J. Synthetic Lubrication., 9:145 (1992); Asadauskas, S. et al.; Lub. Eng., 52:877 (1996)]. Vegetable oil-based derivatives are attractive alternatives to petroleum derived products because they have enhanced biodegradability, lower toxicity and they originate from renewable oilseed sources. The ester linkages deliver inherent lubricity and enable the oils to adhere to metal surfaces. In addition, vegetable oils have higher solubilising capacity for contaminants and additives than mineral oil base fluids. Most of the work reported on lubricant base stocks in the literature is based on edible oils.

A major non-edible oil namely castor oil serves as an industrial raw material for the manufacture of a number of functional derivatives [J. Am. Oil Chem. Soc. 51, 65 (1974), J. Am. Oil Chem. Soc. 48, 759 (1971)]. Castor oil is a well known lubricant due to the presence of hydroxyl fatty acid (12-Hydroxy 9 cis-octadecenoic acid or ricinoleic acid) to an extent of 85-90% (Chemical Business, 1991, 55-60). J. Synthetic Lubrication 24,181 (2007) reported the physico-chemical characteristics of castor oil.

Castor oil has undesirable very high viscosity at 40° C. as well as at 100° C. castor oil also gets dehydrated at temperature of about 200° C. and above.

The rheological characteristics of chemically modified castor oil are much better than mineral oil and other plant oils based lubricants. Castor oil based esters with hydroxyl group at position 12 esterified with $C_6$, $C_{12}$, $C_{16}$ and $C_{18}$ fatty acids are of interest, mainly due to their physical characteristics at low temperature (Eur J Lipid Sci. Technol. 2003, 105, 214-218). Esters with a free hydroxyl group are efficient in improving the lubrication ability of petroleum fuels. Methyl and ethyl esters of ricinoleic and 12-hydroxy octadecanoic acids were prepared and their physico-chemical properties were determined and the results suggested that with the exception of the viscosity, density and cetane number the presence of free hydroxyl group had no influence on their parameters and does not limit the use of their esters as fuels (Eur J. lipid Sci. Technol., 2006, 108, 629-635). Soybean oil was modified to convert sites of unsaturation to $C_2$ to $C_{10}$ diesters which have utility as hydraulic fluids, metal working fluids and other industrial fluids (U.S. Pat. No. 6,583,302). There were no reports on the preparation of derivatives of these tri hydroxy fatty acid rich mixture for their usefulness as lubricant base stocks.

OBJECTS OF THE INVENTION

The main objective of the present invention is to make different lubricant base stocks starting from 9,10,12-trihydroxy octadecanoic acid rich fatty acid mixture.

Another objective of the invention is to convert the 9,10, 12-trihydroxy octadecanoic acid rich fatty acid mixture in to their alkyl esters using linear and branched chain alcohols.

A further objective of the invention is to convert the alkyl esters of 9,10,12-trihydroxy octadecanoic acid rich fatty acid mixture in to their corresponding tri acyloxy derivatives by reacting with acid anhydrides of 2-8 carbon chain length.

It is also an objective of the invention to provide the physico-chemical properties of these esters.

Another objective of the invention is to isolate all the triacyloxy fatty acid alkyl esters from the triacyloxy fatty acid alkyl esters rich products and their structural elucidation by $^1$H NMR studies.

Yet a further objective of the invention is to prepare environmental friendly castor oil-based lubricant base stocks having wide viscosity range and low temperature properties suitable for industrial applications.

SUMMARY OF THE INVENTION

Accordingly the present invention relates to a novel class of chemically modified castor oil based lubricant base stocks as well as methods for producing them. In accordance with the invention, 12-hydroxy 9-cis-octadecenoic acid based lubricant base stocks are prepared starting from castor oil. Accordingly castor oil is dihdroxylated using hydrogen peroxide in the presence of acid catalyst followed by saponification to get a mixture of hydroxy fatty acids and non-hydroxy fatty acids. 9,10,12-Trihydroxy octadecanoic acid is the major fatty acid present in the product.

DETAILED DESCRIPTION

Accordingly, the present invention provides 9,10,12-trihydroxy octadecanoic acid alkyl esters and 9,10,12-triacyloxy octadecanoic acid alkyl esters of general formula 1.

General formula 1

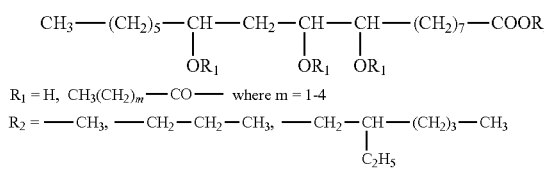

In an embodiment the present invention wherein the compound 9, 10,12-triacyloxy octadecanoic acid alkyl esters are useful as potential lubricant base stocks, preparing lubricant formulations for applications in hydraulic, metal working fluids and other industrial fluids.

Accordingly, the present invention provides a process for preparation of 9,10,12-triacyloxy octadecanoic acid alkyl esters of formula 1 the steps comprising;
(a) adding acetic acid and sulphuric acid to castor oil and followed by addition of hydrogen peroxide 12-20° C. for a period ranging between 2 to 2.5 hr,
(b) pouring the reaction mixture to water and extracting the mixture with water immiscible solvents, like benzene, chloroform and ethylacetate to obtain the residue.
(c) heating the product obtained in step (b) with alkali hydroxide like sodium hydroxide and potassium hydroxide and neutralized with HCl to obtain 9,10,12-trihydroxy octadecanoic acid rich fatty acid mixture
(d) esterification of 9,10,12-hydroxy octadecanoic acid rich fatty acid mixture with alcohol to obtain 9,10,12-trihydroxy octadecanoic acid alkyl esters rich fatty acid alkyl esters mixture,
(e) acylating the 9,10,12-trihydroxy octadecanoic acid alkyl esters rich fatty acid alkyl ester mixture obtained in step (d) with acid anhydride in presence of dimethyl amino pyridine DMAP in a solvent selected from water azeotrope forming solvent like xylene, toluene were used, at a temperature ranging depending on the boiling point of the solvent for a period required for complete conversion to obtain 9,10,12-tri acyloxy octadecanoic acid alkyl ester rich fatty acid alkyl ester mixture, purifying the 9,10,12-triacyloxy octadecanoic acid alkyl esters from the mixture.

In an embodiment the present invention provides a process in which 9,10,12-trihydroxy octadecanoic acid rich fatty acid mixture contains about 87.0% of 9,10,12-trihydroxy octadecanoic acid.

Yet another embodiment the present invention provides a process wherein the alcohols used for esterification of carboxylic group of 9,10,12-trihydroxy octadecanoic acid may be selected from a group consisting of methanol, propanol and 2-ethyl hexanol presence of stannous chloride or sulphuric acid as catalyst in the concentration of 0.1-0.2% and 1-2% respectively.

In an embodiment the present invention provides a process wherein the esterification may be carried out using a molar ratio of fatty acid mixture to alcohol in the range of 1:2 to 1:27.

In another embodiment the present invention provides a process wherein the esterification reaction may be carried out in the temperature range of 60 to 190° C.

In another embodiment the present invention provides a process wherein the esterification reaction may be carried out for a time period in the range of 6-8 hours.

In an embodiment of the present invention wherein anhydrides used for acylation of hydroxyl groups of 9,10,12-trihydroxy octadecanoic acid may be selected form a group consisting of propionic, butyric, valeric and hexanoic anhydrides in presence of DMAP in the concentration of 0.1% at 175 to 180° C.

In an embodiment the present invention provides a process wherein 9,10,12-tri acyloxy octadecanoic acid alkyl ester rich fatty acid alkyl ester mixture may be useful as potential lubricant base stocks, preparing lubricant formulations for applications in hydraulic, metal working fluids and other industrial fluids.

In an embodiment the present invention provides a process wherein 9,10,12-triacyloxy octadecanoic acid alkyl esters are isolated from the 9,10,12-triacyloxy octadecanoic acid alkyl esters rich product and elucidated their structure by $^1$H NMR.

In an embodiment the present invention provides a process wherein the 9,10,12-triacyloxy octadecanoic acid alkyl esters can also be prepared from the readily available 9,10,12-trihydroxy octadecanoic acid by esterfication followed by acylation.

Vegetable oils like castor oil have been used as lubricants since ancient times. These materials, similar to synthetic esters, have better biodegradability than mineral oils and are also renewable. Vegetable oils have some shortcomings, such as a higher pour point and a lower viscosity index than synthetic esters. They have a limited viscosity range and lower oxidative stability due to the presence of unsaturated bonds. Therefore vegetable oils as such cannot satisfy all the requirements of modern machine lubrication. Hence, in the present invention, the chemical structure of natural castor oil is modified by chemical modification to octadecanoic acid triesters. 9,10,12-Trihydroxy octadecanoic acid rich fatty acid mixture was prepared from castor oil and converted to their alkyl esters followed by acylation of hydroxy groups to get 9,10,12-triacyloxy octadecanoic acid alkyl ester rich fatty acid alkyl esters mixture. The products were evaluated for acid value (A.V.), hydroxyl value (H.V.), iodine value (I.V.), viscosity, viscosity index (V.I.), pour point, flash point and copper strip corrosion and found to be potential base stocks for hydraulic, metal working fluids and other industrial fluids. The viscosity and pour point characteristics of 9,10,12-triacyloxy octadecanoic acid alkyl ester rich fatty acid alkyl esters mixture were superior to castor oil.

According to the present invention, castor oil with 87.0% ricinoleic acid (12-hydroxy 9 cis-octadecenoic acid) is epoxidised and the epoxy ring was opened in situ with acetic acid followed by saponification with alkali followed by neutralization to get 9,10,12-trihydroxy octadecanoic acid rich fatty acid mixture.

In the next step, the carboxylic groups of the 9,10,12-trihydroxy octadecanoic acid rich fatty acid mixture is converted in to their alkyl esters using linear and branched chain alcohols ($C_1$ to $C_8$) in presence of an acid catalyst.

In an embodiment of the present invention an efficient process is developed for the preparation of 9,10,12-triacyloxy octadecanoic acid alkyl esters rich fatty acid alkyl esters mixture from 9,10,12-trihydroxy octadecanoic acid alkyl esters mixture by reacting with acid anhydrides ($C_3$-$C_6$). The structure of the major constituent namely 9,10,12-trihydroxy octadecanoic acid alkyl esters and 9,10,12-triacyloxy octadecanoic acid alkyl esters present in the product is as follows:

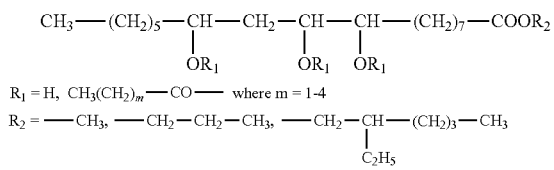

The triacyloxy derivatives were evaluated for their physico-chemical characteristics such as acid value (A.V.), hydroxyl value (H.V.), iodine value (I.V.), viscosity, viscosity index (V.I.), pour point, flash point and copper strip corrosion. The triacyloxy derivatives exhibit properties which render them useful as base stocks for biodegradable lubricant applications like hydraulic fluids, metal working fluids and other industrial fluids. Certain properties of these products meet or exceed some specifications for some lubricant applications without the addition of conventional additives.

The following examples are intended to further illustrate the invention, without any intent for the invention to be limited to the specific embodiments described therein.

EXAMPLE 1

Preparation of methyl esters of 9,10,12-trihydroxy octadecanoic acid rich fatty acids Castor oil (200 g) was taken in 2 lit R.B. flask and to this glacial acetic acid (700 g), and sulphuric acid (13.3 g) were added and the reaction mixture was cooled to 15-20° C. To the cooled stirred suspension, 50% hydrogen peroxide (393 g) was added drop wise over a period of 2 hr. After complete addition of hydrogen peroxide, the temperature of the reaction mixture was slowly raised to 40° C. and allowed to stir for additional 5 hr. At the end or reaction time the contents were poured in to cold water and left it over night. The organic phase was extracted with ethyl acetate (2×1000 ml) and the ethyl acetate extract was washed with water till the pH of aq. phase was neutral. The ethyl acetate extract was passed through a bed of anhydrous sodium sulphate and the solvent was removed using rota vapour to recover the intermediate product (260 g) after drying under vacuum. The intermediate product (260 g) was taken into a 5 lit R.B. flask and to this added 3N sodium hydroxide solution (2666 ml) and stirred mechanically for 2 hr at 80° C. After 2 hr the contents were neutralized with 1:1 aq. HCl (800 ml) and the temperature of the suspension was brought down to around 30° C. and stirred for additional 20 min. The precipitate was filtered and dried in a vacuum desiccator to recover 9,10,12-trihydroxy octadecanoic acid rich fatty acid mixture (150 g). This product was taken in 2 lit R.B.flask and to this added 2% sulphuric acid in methanol (500 ml) and the contents were stirred at 60° C. for 6 hr. The course of the reaction was monitored by determining acid value at regular intervals. After completion of reaction part of methanol was evaporated using rotavapor and the residue was taken in ethyl acetate (1 lit) and washed with distilled waster (5×250 ml) till neutral pH. The ethyl acetate extract was passed through a bed of anhydrous sodium sulphate and concentrated and vacuum dried to recover the product (120 g) having an A.V. of 2.2, H.V. 460 and I.V. of 2.0.

Methyl esters of 9,10,12-trihydroxy octadecanoic acid was purified by column chromatography and the structure of the title product was established by $^1$H studies.

$^1$H NMR (CDCl$_3$, δ ppm): 0.9 [t, —CH$_3$], 1.2-1.7 [m, 12×—CH$_2$—], 2.3 [t, —CO—CH$_2$—], 3.5-3.9 [m, 3×(—C$\underline{\text{H}}$—OH), —O—CH$_3$].

EXAMPLE 2

Preparation of 9,10,12-tripropoxy octadecanoic acid methyl ester rich fatty acid methyl esters mixture 9,10,12-Trihydroxy octadecanoic acid rich fatty acid methyl esters (300 g) as prepared in example 1 was taken in one lit R.B.Flask and to this added propanoic anhydride (681 g), Dimethyl amino pyridine (DMAP, 300 mg) and xylene (100 ml) and stirred the contents magnetically at 180° C. for 6 hr. The course of the reaction was monitored by TLC. After completion of the reaction xylene and unconverted propanoic anhydride and propanoic acid were distilled under reduced pressure and the residue was taken in ethyl acetate. The ethyl acetate extract was washed with distilled water and passed through anhydrous sodium sulphate and concentrated under vacuum to recover the product (270 g) having an A.V. of 0.3, H.V. of 3.3 and I.V. of 2.0. The product was evaluated for viscosity, viscosity index (V.I.), pour point, flash point and copper strip corrosion and the data is provided in the following table.

| Property | Value |
| --- | --- |
| Viscosity at 40° C. cSt | 32.42 |
| Viscosity at 100° C. cSt: | 5.18 |
| Viscosity Index | 84 |
| Pour Point (° C.) | −33 |
| Flash point (° C.) | 252 |
| Copper strip corrosion | 1 a |

9,10,12-Tripropoxy octadecanoic acid methyl ester was purified by column chromatography and the structure of the title product was established by $^1$H studies.

$^1$H NMR (CDCl$_3$, δ ppm): 0.9 [t, —CH$_3$], 1.1-1.8 [m, 12×—CH$_2$, 3×—CH$_3$], 2.2-2.4 [m, 4×(—CO—CH$_2$—)], 3.6 [s, —O—CH$_3$], 4.8-5.2 [m, 3×(—O—C$\underline{\text{H}}$)].

EXAMPLE 3

Preparation of 9,10,12-tributyroxy octadecanoic acid methyl ester rich fatty acid methyl esters mixture The title compound (190 g) was prepared by reacting 9,10,12-Trihydroxy octadecanoic acid methyl ester rich fatty, acid methyl esters mixture (97 g) with butyric anhydride (260 g) according experiment 2 having an A.V. of 0.1, H.V. of 2.4 and I.V. of 2.0. The product was evaluated for viscosity, viscosity index (V.I.), pour point, flash point and copper strip corrosion and the data is provided in the following table.

| Property | Value |
| --- | --- |
| Viscosity at 40° C. cSt | 24.2 |
| Viscosity at 100° C. cSt: | 4.66 |
| Viscosity Index | 109 |
| Pour Point (° C.) | −42 |
| Flash point (° C.) | 252 |
| Copper strip corrosion | 1 a |

9,10,12-Tributyroxy octadecanoic acid methyl ester was purified by column chromatography and the structure of the title product was established by $^1$H studies. $^1$H NMR (CDCl$_3$, δ ppm): 0.9 [m, 4×(—CH$_3$)], 1.2-1.8 [m, 15×—CH$_2$—], 2.2-2.3 [m, 4×(—CO—CH$_2$—)], 3.6 [s, —O—CH$_3$], 4.8-5.2 [m, 3×(—O—CH)].

EXAMPLE 4

Preparation of 9,10,12-trivaleroxy octadecanoic acid methyl ester rich fatty acid methyl esters mixture The title compound (210 g) was prepared by reacting 9,10,12-Trihydroxy octadecanoic acid methyl ester rich fatty acid methyl esters mixture (90 g) with valeric anhydride (352 g) according to experiment 2 having an A.V. of 0.3, H.V. of 1.9 and I.V. of 2.0. The product was evaluated for viscosity, viscosity index (V.I.), pour point, flash point and copper strip corrosion and the data is provided in the following table.

| Property | Value |
| --- | --- |
| Viscosity at 40° C. cSt | 12.63 |
| Viscosity at 100° C. cSt: | 3.21 |
| Viscosity Index | 129 |
| Pour Point (° C.) | −54 |

-continued

| Property | Value |
| --- | --- |
| Flash point (° C.) | 252 |
| Copper strip corrosion | 1 a |

9,10,12-Trivaleroxy octadecanoic acid methyl ester was purified by column chromatography and the structure of the title product was established by $^1$H studies.

$^1$H NMR (CDCl$_3$, δ ppm): 0.8-1.0 [m, 4×—CH$_3$], 1.2-1.7 [m, 18×—CH$_2$—], 2.2-2.4 [m, 4×—CO—CH$_2$—], 3.6 [s, —O—CH$_3$], 4.8-5.2 [m, 3×(—O—CH)].

EXAMPLE 5

Preparation of 9,10,12-trihexyloxy octadecanoic acid methyl ester rich fatty acid methyl esters mixture The title compound (113 g) was prepared by reacting 9,10,12-Trihydroxy octadecanoic acid methyl ester rich fatty acid methyl esters mixture (45 g) with hexanoic anhydride (162 g) according to experiment 2 having an A.V. of 0.3, H.V. of 2.0 and I.V. of 2.0. The product was evaluated for viscosity, viscosity index (V.I.), pour point, flash point and copper strip corrosion and the data is provided in the following table.

| Property | Value |
| --- | --- |
| Viscosity at 40° C. cSt | 35.37 |
| Viscosity at 100° C. cSt: | 6.2 |
| Viscosity Index | 127 |
| Pour Point (° C.) | −39 |
| Flash point (° C.) | 252 |
| Copper strip corrosion | 1 a |

9,10,12-trihexyloxy octadecanoic acid methyl ester was purified by column chromatography and the structure of the title product was established by $^1$H studies.

$^1$H NMR (CDCl$_3$, δ ppm): 0.9-1.0 [m, 4×—CH$_3$], 1.2-1.4 [m, 21×—CH$_2$—], 2.2-2.4 [m, 4×—CO—CH$_2$—], 3.6 [s, —O—CH$_3$], 4.8-5.1 [m, 3×—O—CH].

EXAMPLE 6

Preparation of propyl esters of 9,10,12-trihydroxy octadecanoic acid rich fatty acid mixture 9,10,12 -Trihydroxy octadecanoic acid rich fatty acids mixture (400 g) as prepared in example 1 was taken in one lit. R.B. flask and to this added 1-propanol (108 g) and stannous chloride (400 mg) and the contents were stirred at 96° C. over a period of 8 hr. The course of the reaction was monitored by determining acid value at regular intervals. After completion of reaction, part of 1-propanol was evaporated using rota vapour and the residue was taken in ethyl acetate (600 ml) and washed with distilled water (5×500 ml). The ethyl acetate extract was passed through a bed of anhydrous sodium sulphate, concentrated and vacuum dried and the concentrate was passed through basic alumina column to recover the product (405 g) having an A.V. of 2.5, H.V. 420 and I.V. of 5.0

Propyl esters of 9,10,12-trihydroxy octadecanoic acid was purified by column chromatography and the structure of the title product was established by $^1$H studies.

$^1$H NMR (CDCl$_3$, δ ppm): 0.9-1.0 [m, 2×—CH$_3$], 1.2-1.7 [m, 13×—CH$_2$—], 2.3 [t, —CO—CH$_2$—], 3.3-3.4, 3.5-3.7, 3.7-3.9 [3 m, 3×—CH—OH], 4.0 [t, —O—CH$_2$—].

EXAMPLE 7

Preparation of 9,10,12-tripropoxy octadecanoate propyl ester rich fatty acid propyl ester mixture 9,10,12-Trihydroxy octadecanoic acid propyl ester rich fatty acid propyl esters (200 g) as prepared in example 6 was taken in one lit R.B. Flask and to this added propanoic anhydride (313.6 g), DMAP (200 mg) and xylene (100 ml) and stirred the contents magnetically at 130° C. for 6 hr. The course of the reaction was monitored by TLC. After completion of the reaction xylene and unconverted propanoic anhydride and propanoic acid were distilled under reduced pressure and the residue was taken in ethyl acetate (600 ml). The ethyl acetate extract was washed with distilled water and passed through anhydrous sodium sulphate and concentrated under vacuum and the concentrate was passed through basic alumina column to recover the product (190 g) having an A.V. of 0.3, H.V. of 0.5 and I.V. of 5.0. The product was evaluated for viscosity, viscosity index (V.I.), pour point, flash point and copper strip corrosion and the data is provided in the following table.

| Property | Value |
| --- | --- |
| Viscosity at 40° C. cSt | 40.57 |
| Viscosity at 100° C. cSt: | 6.38 |
| Viscosity Index | 106 |
| Pour Point (° C.) | −18 |
| Flash point (° C.) | 228 |
| Copper strip corrosion | 1 a |

9,10,12-Tripropoxy octadecanoate propyl ester was purified by column chromatography and the structure of the title product was established by $^1$H studies.

$^1$H NMR (CDCl$_3$, δ ppm): 0.8-1.0 [m, 5×—CH$_3$], 1.1-1.7 [m, 13×—CH$_2$—], 2.2-2.4 [m, 4×—CO—CH$_2$—], 4.0 [t, —O—CH$_2$—], 4.8-5.2 [m, 3×—O—CH—].

EXAMPLE 8

Preparation of 9,10,12-trivaleroxy octadecanoic acid propyl ester rich fatty acid propyl ester mixture 9,10,12-Trihydroxy octadecanoic acid propyl ester rich fatty acid propyl esters (200 g) as prepared in example 6 was taken in one lit R.B. Flask and to this added valeric anhydride (447 g), DMAP (200 mg) and xylene (100 ml) and stirred the contents magnetically at 180° C. for 6 hr. The course of the reaction was monitored by TLC. After completion of the reaction xylene and unconverted valeric anhydride and valeric acid were distilled under reduced pressure and the residue was taken in ethyl acetate (600 ml). The ethyl acetate extract was washed with distilled water and passed through anhydrous sodium sulphate and concentrated under vacuum and the concentrate was passed through basic alumina column to recover the product (198 g) having an A.V. of 0.2, H.V. of 0.7 and I.V. of 5.0. The product was evaluated for viscosity, viscosity index (V.I.), pour point, flash point and copper strip corrosion and the data is provided in the following table.

| Property | Value |
| --- | --- |
| Viscosity at 40° C. cSt | 44.51 |
| Viscosity at 100° C. cSt: | 7.2 |
| Viscosity Index | 126 |
| Pour Point (° C.) | −24 |
| Flash point (° C.) | 238 |
| Copper strip corrosion | 1 a |

9,10,12-Trivaleroxy octadecanoic acid propyl ester was purified by column chromatography and the structure of the title product was established by $^1$H studies.

$^1$H NMR (CDCl$_3$, δ ppm): 0.85-1.0 [m, 5×—CH$_3$], 1.2-1.7 [m, 19×—CH$_2$—], 2.2-2.4[m, 4×—CO—CH$_2$—], 4.0 [t, —O—CH$_2$—], 4.8-5.2 [m, 3×—O—CH-].

EXAMPLE 9

Preparation of 2-ethylhexyl esters of 9,10,12-trihydroxy octadecanoic acid rich fatty acid mixture 9,10,12-Trihydroxy octadecanoic acid rich fatty acid mixture (200 g) was taken in one lit R.B. flask and to this 2-ethylhexanol (156 g), stannous chloride (200 mg) and xylene (100 ml) were added and the contents were stirred magnetically at 190° C. for 8 hr. The course of the reaction was monitor by TLC. After completion of reaction excess 2-ethylhexanol, xylene were distilled under reduced pressure. The residue was taken in ethyl acetate (600 ml) and the organic layer was water washed till neutral pH. The solvent was evaporated using rotavapor to recover the product (180 g) having an A.V. of 0.9 and I.V. of 5.0.

2-Ethylhexyl esters of 9,10,12-trihydroxy octadecanoic acid was purified by column chromatography and the structure of the title product was established by $^1$H studies.

$^1$H NMR (CDCl$_3$, δ ppm): 0.8-0.9 [m, 3×—CH$_3$], 1.1-1.7 [m, 16×—CH$_2$—], 2.3 [t, —CO—CH$_2$—], 3.6 [m, —CH—OH], 3.7 [m, —OCH$_2$—], 4.2-4.3 [m, 2×—CH—OH].

EXAMPLE 10

Preparation of 9,10,12-tripropoxy octadecanoic acid 2-ethylhexyl ester rich fatty acid 2-ethylhexyl ester mixture 9,10,12-Tri hydroxy octadecanoic acid 2-ethylhexyl ester rich fatty acid 2-ethylhexyl esters (150 g) as prepared in example 9 was taken in one lit R.B. flask and to this propanoic anhydride (257 g), dimethyl amino pyridine (150 mg) and xylene (100 ml) were added and the contents stirred magnetically at 180° C. for 6 hr. The course of the reaction was monitored by TLC. After completion of the reaction xylene and unconverted propanoic anhydride and propanoic acid were distilled under reduced pressure and the residue was taken in ethyl acetate. The ethyl acetate extract was washed with distilled water and passed through anhydrous sodium sulphate and concentrated under vacuum to recover the product (257 g). The product had an A.V. of 0.9, H.V. of 1.5 and I.V. of 5.0. The product was evaluated for viscosity, viscosity index (V.I.), pour point, flash point and copper strip corrosion and the data is provided in the following table.

| Property | Value |
| --- | --- |
| Viscosity at 40° C. cSt | 76.22 |
| Viscosity at 100° C. cSt: | 10.62 |
| Viscosity Index | 125 |
| Pour Point (° C.) | −30 |
| Flash point (° C.) | 262 |
| Copper strip corrosion | 1 a |

9,10,12-tripropoxy octadecanoic acid 2-ethylhexyl ester was purified by column chromatography and the structure of the title product was established by $^1$H studies. $^1$H NMR (CDCl$_3$, δ ppm): 0.8-0.9 [m, 6×—CH$_3$], 1.1-1.7 [m, 16×—CH$_2$—], 2.3-2.4 [m, 4×—CO—CH$_2$—], 3.9 [m, —O—CH$_2$—], 4.8-5.2 [m, 3×—O—CH—]

Advantages of the Invention

In the present patent novel chemically modified castor oil fatty acid derivatives were prepared having superior lubricant performance characteristics. These products exhibited good viscosity index high flash point and very low pour points. They will have superior thermal and oxidative stabilities due to lack of unsaturation. They are potential base stocks for metal working, hydraulic and other industrial fluids.

We claim:

1. 9,10,12-Trihydroxy octadecanoic acid alkyl esters and 9,10,12-triacyloxy octadecanoic acid alkyl esters of general formula 1

General formula 1

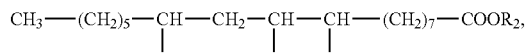

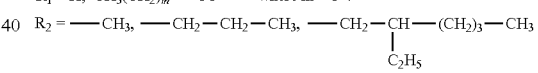

such that when R1=H, then R2 is not CH$_3$.

2. 9,10,12-triacyloxy octadecanoic acid alkyl esters as claimed in claim 1 of general formula 1

General formula 1

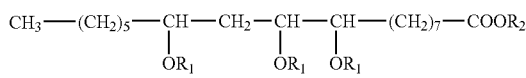

where

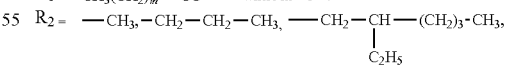

3. 9,10,12- trihydroxy octadecanoic acid alkyl esters as claimed in claim 1 of general formula 1

General formula 1

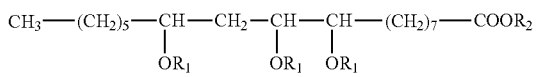

where
R₁ = H

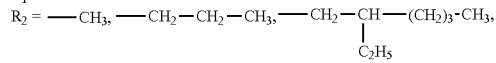

such that when R1=H, then R2 is not CH₃.

4. A process for preparation of 9,10,12-triacyloxy octadecanoic acid alkyl esters of formula 1 as claimed in claim 1 wherein the steps comprising;
(a) adding acetic acid and sulphuric acid to castor oil and followed by addition of hydrogen peroxide 12-20° C. for a period ranging between 2 to 2.5 hr,
(b) pouring the reaction mixture to water and extracting the mixture with water immiscible solvent to obtain the residue,
(c) heating the product obtained in step (b) with alkali hydroxide and neutralized with HC 1 to obtain 9,10,12-trihydroxy octadecanoic acid rich fatty acid mixture
(d) esterification of 9,10,12-trihydroxy octadecanoic acid rich fatty acid mixture with alcohol to obtain 9,10,12-trihydroxy octadecanoic acid alkyl esters rich fatty acid alkyl esters mixture,
(e) acylating the 9,10,12-trihydroxy octadecanoic acid alkyl esters rich fatty acid alkyl ester mixture obtained in step (d) with acid anhydride in presence of dimethly amino pyridine DMAP in a temperature ranging depending on the boiling point of the solvent for a period required for complete conversion to obtain 9,10,12-tri acyloxy octadecanoic acid alkyl ester rich fatty acid alkyl ester mixture, purifying the 9,10,12-triacyloxy octadecanoic acid alkyl esters from the mixture.

5. A process as claimed in claim 4, wherein 9,10,12-trihydroxy octadecanoic acid rich fatty acid mixture contains about 87.0% of 9,10,12-trihydroxy octadecanoic acid.

6. A process as claimed in claim 4, wherein the alcohols used for esterification of carboxylic group of 9,10,12-trihydroxy octadecanoic acid is selected from a group consisting of methanol, propane! and 2-ethyl hexanol in presence of stannous chloride or sulphuric acid as catalyst in the concentration of 0.1.0.2% and 1-2% respectively.

7. A process as claimed in claim 4, wherein the esterification is carried out using a molar ratio of fatty acid mixture to alcohol in the range of 1:2 to 1: 27.

8. A process as claimed in claim 4, wherein the esterification reaction is carried out in the temperature range of 60 to 190° C.

9. A process as claimed in claim 4, wherein the esterification reaction is carried out for a time period in the range of 6-8 hours.

10. A process as claimed in claim 4, wherein the anhydrides used for acylation of hydroxyl groups of 9,10,12 -trihydroxy octadecanoic acid is selected form a group consisting of propionic, butyric, valeric and hexanoic anhydrides in presence of DMAP in the concentration of 0.1% at 175 to 180° C.

11. A process as claimed in claim 4, wherein 9,10,12-triacyloxy octadecanoic acid alkyl ester rich fatty acid alkyl ester mixture is useful as potential lubricant base stocks, preparing lubricant formulations for applications in hydraulic, metal working fluids and other industrial fluids.

12. A process as claimed in claim 4, wherein the 9,10,12-triacyloxy octadecanoic acid alkyl esters are isolated from the 9,10,12-triacyloxy octadecanoic acid alkyl esters rich product and elucidated their structure by 'H NMR.

* * * * *